(12) United States Patent
Kleiner et al.

(10) Patent No.: US 8,182,829 B2
(45) Date of Patent: May 22, 2012

(54) DRUG ELUTING IMPLANTABLE MEDICAL DEVICE WITH HEMOCOMPATIBLE AND/OR PROHEALING TOPCOAT

(75) Inventors: Lothar W. Kleiner, Los Altos, CA (US); Yiwen Tang, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 671 days.

(21) Appl. No.: 11/881,668

(22) Filed: Jul. 27, 2007

(65) Prior Publication Data
US 2009/0030505 A1    Jan. 29, 2009

(51) Int. Cl.
*A61F 2/00*    (2006.01)
*A61K 9/14*    (2006.01)
*A61K 38/00*   (2006.01)

(52) U.S. Cl. .......................... 424/423; 424/486; 514/1.1

(58) Field of Classification Search .................. None
See application file for complete search history.

(56) References Cited

U.S. PATENT DOCUMENTS

| | | | |
|---|---|---|---|
| 4,485,227 A | 11/1984 | Fox | |
| 5,477,864 A | 12/1995 | Davidson | |
| 5,811,447 A * | 9/1998 | Kunz et al. | 514/411 |
| 6,153,252 A * | 11/2000 | Hossainy et al. | 427/2.3 |
| 6,284,854 B1 | 9/2001 | Bowers et al. | |
| 7,201,962 B2 | 4/2007 | Albright | |
| 2006/0088571 A1 | 4/2006 | Chen et al. | |
| 2006/0093771 A1 * | 5/2006 | Rypacek et al. | 428/36.91 |
| 2007/0026037 A1 | 2/2007 | Kloke et al. | |
| 2007/0149640 A1 * | 6/2007 | Andjelic et al. | 523/105 |
| 2007/0160848 A1 | 7/2007 | Albright et al. | |

FOREIGN PATENT DOCUMENTS

| | | | |
|---|---|---|---|
| EP | 1832289 | | 9/2007 |
| WO | WO 2005/082430 | * | 9/2005 |
| WO | WO 2007/024492 | | 3/2007 |

OTHER PUBLICATIONS

Ghanashyam Acharya et. al., Mechanisms of Controlled drug release from drug eluting stents, Advanced Drug Delivery Reviews 58 (2006) 387-401, available online Mar. 6, 2006.*

Kidane, Asmeret G. et. al., Incorporation of a lauric acid conjugated GRGDS peptide directly into the matrix of a poly(carbonate-urea) urethane polymer for use in cardiovascular bypass graft applications, Journal of Biomedical Materials Research Part 79A, published Jul. 6, 2006, pp. 606-617.*
Noga, David E., et al., Synthesis and Modification of Functional Poly(lactide) Copolymers: Toward Biofunctional Materials, Biomacromolecules, 2008, 9, 2056-2062.*
Jee, Kyoung Soo, et al., Biomacromolecules 2004, 5, 1877-1881.*
Whitaker-Brothers, Kenya, et al., J Biomed Mater Res 76A: 470-479, 2006.*
Blindt et al., "Abciximab Inhibits the Migration and Invasion Potential of Human Coronary Artery Smooth Muscle Cells", J. Mol. Cell Cardiol. 32, pp. 2195-2206 (2000).
Coller, "Anti-GPIIb/IIIa Drugs: Current Strategies and Future Directions", Thromb Haemost 86, pp. 427-443 2001).
Fittkau et al., "The selective modulation of endothelial cell mobility on RGD peptide containing surface by YIGSR peptides", Biomaterials 26, pp. 167-174 (2005).
Kouvroukoglou et al, "Endothelial cell migration on surfaces modified with immobilized adhesive peptides", Biomaterials 21, pp. 1725-1733 (2000).
Mann et al., "Cell adhesion peptides alter smooth muscle cell adhesion, proliferation, migration, and matrix protein synthesis on modified surfaces and in polymer scaffolds", Ed. By John Wiley & Sons, Inc. pp. 86-93 (2002).
Sajid et al., "$\alpha v \beta 3$—Integrin antagonists inhibit thrombin-induced proliferation and focal adhesion formation in smooth muscle cells", Am. J. Physiol 285, pp. C1330-C1338 (2003).
Schatz et al., "Clinical Experience with the Palmaz-Schatz Coronary Stent", Circulation vol. 83, No. 1, pp. 148-161 (1991).
International Search Report for PCT/US2008/068850, mailed Jan. 15, 2010, 23 pgs.
Invitation to Pay Additional Fees for PCT/US2008/068850, mailed Oct. 2, 2009, 10 pgs.
Gerhardt et al., "Functional lactide Monomers: Methodology and Polymerization", Biomacromolecules 7, pp. 1735-1742 (2006).
Leemhuis et al., "Functionalized Poly($\alpha$-hydroxy acid)s via Ring-Opening Polymerization: Toward Hydrophilic Polyesters with Pendant Hydroxyl Groups", Macromolecules 39, pp. 3500-3508 (2006).
European Search Report for appl. No. 08 796 059.7, mailed Dec. 3, 2010, 5 pgs.

* cited by examiner

*Primary Examiner* — Kevin Hill
*Assistant Examiner* — Lyndsey Beckhardt
(74) *Attorney, Agent, or Firm* — Squire Sanders (US) LLP

(57) ABSTRACT

The present invention relates to implantable medical devices coated with polymer having hemocompatible and/or prohealing moieties appended thereto and to their use in the treatment of vascular diseases.

3 Claims, No Drawings

DRUG ELUTING IMPLANTABLE MEDICAL DEVICE WITH HEMOCOMPATIBLE AND/OR PROHEALING TOPCOAT

FIELD OF THE INVENTION

This invention relates to the fields of organic chemistry, polymer science, material science and medical devices. In particular, it relates to a medical device having a bioabsorbable coating with hemocompatible and/or prohealing moieties for treating vascular diseases.

BACKGROUND OF THE INVENTION

Percutaneous transluminal coronary angioplasty (PTCA) is a common procedure for treating heart disease. A problem associated with the PTCA includes the formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of thrombosis and restenosis, a stent may be implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Biological therapy can be achieved by medicating the stents, in particular by using drug-eluting stents, DESs. DESs can provide local administration of a therapeutic substance at the specific site in an patient's body. This can result in fewer and less severe side effects and more favorable overall results.

The early use of coronary stents to improve the long-term patency of an artery post-angioplasty was, however, complicated by a high incidence of subacute thrombosis (SAT) (R.A. Schatz et al., *Circulation* 1991, 83: 148-161). Despite improved pharmacological control of SAT, the potential for stent occlusion remains a serious problem. In addition, with the advent of DESs a new problem arose: late stent thrombosis, the forming of blood clots long after the stent is in place. It was deduced that the formation of blood clots was most likely due to delayed healing which was postulated to be a side-effect of the use of cytostatic drugs.

Delayed healing and polymer degradation have also been associated with stent malapposition, and hypersensitivity reactions.

What is needed is an implantable medical device that has improved hemocompatibility and/or prohealing properties to ameliorate, if not eliminate, subacute thrombosis, late stent thrombosis and other problems associated with delayed healing. The current invention provides such implantable medical devices.

SUMMARY OF THE INVENTION

Thus, in one aspect, the current invention relates to an implantable medical device, comprising:

a device body;
an optional primer layer disposed over the device body;
a drug reservoir layer disposed over the device body or the primer layer, if opted,
wherein the drug reservoir layer comprises:
   a high molecular weight copolymer of lactic acid, L-lactide, D,L-lactide or meso-lactide with ε-caprolactone or trimethylene carbonate, at least a portion of which is substituted with a hemocompatible and/or prohealing moiety; or,
   a blend of a high molecular weight copolymer of lactic acid, L-lactide, D,L-lactide or meso-lactide with ε-caprolactone or trimethylene carbonate with a low molecular weight copolymer of lactic acid, L-lactide, D,L-lactide or meso-lactide with ε-caprolactone or trimethylene carbonate at least a portion of which is substituted with a hemocompatible and/or prohealing moiety; or, a high molecular weight copolymer of lactic acid, L-lactide, D,L-lactide or meso-lactide with ε-caprolactone or derivatives thereof; and,
one or more therapeutic agents, wherein:
   if the drug reservoir layer comprises only a high molecular weight copolymer of lactic acid, L-lactide, D,L-lactide or meso-lactide with ε-caprolactone or trimethylene carbonate, the implantable medical device further comprises a topcoat layer comprising a low molecular weight copolymer of lactic acid, L-lactide, D,L-lactide or meso-lactide with ε-caprolactone or trimethylene carbonate at least a portion of which is substituted with a hemocompatible and/or prohealing moiety.

In an aspect of this invention, the implantable medical device is a stent.

In an aspect of this invention, the hemocompatible and/or prohealing moiety comprises a polyhydroxyalkyl.

In an aspect of this invention, the drug reservoir layer or the topcoat layer comprises a polyhydroxyalkyl moiety having the formula:

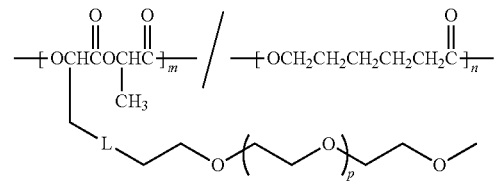

wherein L comprises a Linker; m and n have values from 0 to 1, wherein m+n=1; and p is an integer from 1 to 200.

In an aspect of this invention, the polyhydroxyalkyl is selected from the group consisting of glycerol, sorbitol, mannitol, a glycol, a polyalkylglycol and a polyglycol.

In an aspect of this invention, the hemocompatible and/or prohealing moiety comprises a peptide.

In an aspect of this invention, the drug reservoir layer or the topcoat layer comprises a peptide moiety having the formula:

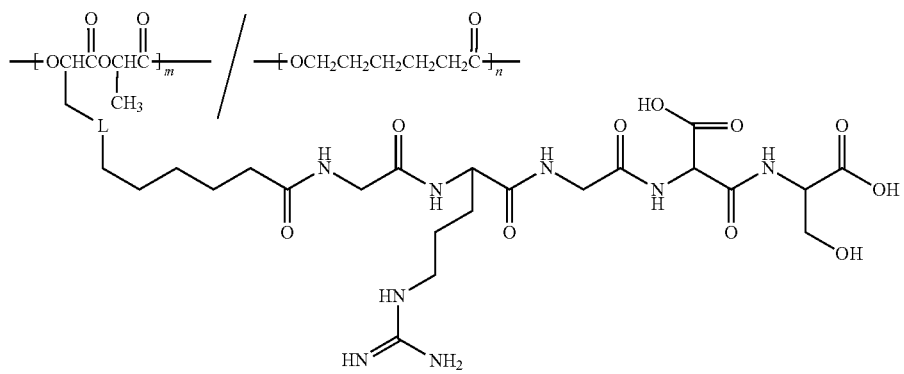

wherein L comprises a Linker and m and n have values from 0 to 1 wherein m+n=1.

In an aspect of this invention, the peptide is selected from the group consisting of RGD, cyclic RGD (cRGD) and an RDG mimetic.

In an aspect of this invention the hemocompatible and/or prohealing moiety comprises a phosphorylcholine.

In an aspect of this invention, the drug reservoir layer or the topcoat layer comprises a phosphorylcholine moiety having the formula:

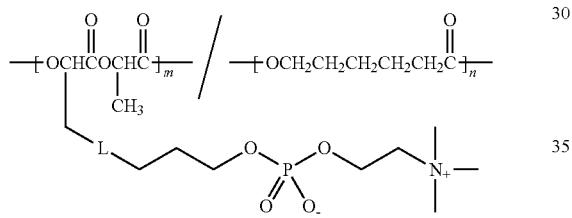

wherein L comprises a Linker and m and n have values from 0 to 1 such that m+n=1.

In an aspect of this invention, the drug reservoir layer polymer has a molecular weight from about 50,000 to about 500,000 Daltons.

In an aspect of this invention, the drug reservoir layer has a coating thickness from about 1 um to about 10 um.

In an aspect of this invention, the drug to polymer wt/wt ratio in the drug reservoir layer is from about 1.0:0.5 to about 1.0:10.0.

In an aspect of this invention, the drug dose is from about 5-200 microgram/cm² to about 20-100 microgram/cm².

An aspect of this invention is a method of treating a vascular disease, comprising: deploying in the vasculature of a patient in need thereof an implantable medical device, wherein the device comprises:
a device body;
an optional primer layer disposed over the device body;
a drug reservoir layer disposed over the device body or the primer layer, if opted,
wherein the drug reservoir layer comprises:
  a high molecular weight copolymer of lactic acid, L-lactide, D,L-lactide or meso-lactide with ε-caprolactone or trimethylene carbonate, at least a portion of which is substituted with a hemocompatible and/or prohealing moiety; or,
  a blend of a high molecular weight copolymer of lactic acid, L-lactide, D,L-lactide or meso-lactide with ε-caprolactone or trimethylene carbonate and a low molecular weight copolymer of lactic acid, L-lactide, D,L-lactide or meso-lactide with ε-caprolactone or trimethylene carbonate at least a portion of which is substituted with a hemocompatible and/or prohealing moiety; or, a high molecular weight copolymer of lactic acid, L-lactide, D,L-lactide or meso-lactide with ε-caprolactone or trimethylene carbonate; and one or more therapeutic agents,
wherein:
  if the drug reservoir layer comprises only a high molecular weight copolymer of lactic acid, L-lactide, D,L-lactide or meso-lactide with ε-caprolactone or trimethylene carbonate, the implantable medical device further has a topcoat layer comprising a low molecular weight copolymer of lactic acid, L-lactide, D,L-lactide or meso-lactide with ε-caprolactone or trimethylene carbonate at least a portion of which is substituted with hemocompatible and/or prohealing moiety.

In an aspect of this invention, the implantable medical device is a stent.

In an aspect of this invention, the hemocompatible and/or prohealing moiety comprises a polyhydroxyalkyl.

In an aspect of this invention, the drug reservoir layer or the topcoat layer comprises a polyhydroxyalkyl moiety having the formula:

wherein L comprises a Linker, m and n have values from 0 to 1 such that m=n=1 and p is an integer from 1 to about 200.

In an aspect of this invention, the polyhydroxyalkyl is selected from the group consisting of glycerol, sorbitol, mannitol, a glycol, a polyalkylglycol and a polyglycol.

In an aspect of this invention, the hemocompatible and/or prohealing moiety comprises a peptide.

In an aspect of this invention, the drug reservoir layer or the topcoat layer comprises a peptide moiety having the formula:

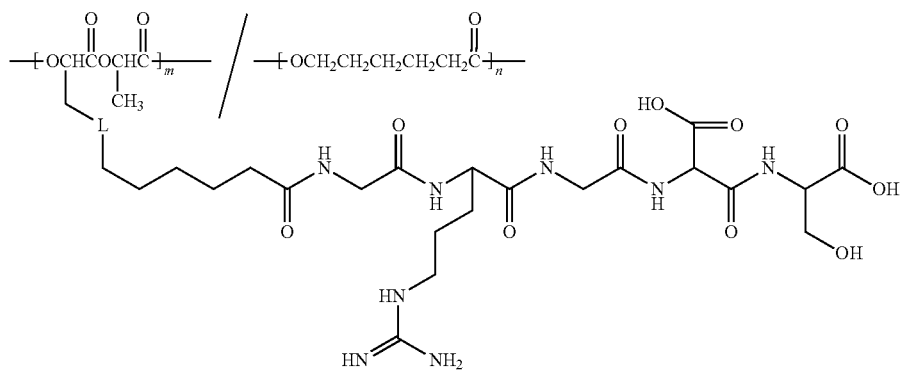

wherein L comprises a Linker and m and n have values from 0 to 1 such that m+n=1.

In an aspect of this invention, the peptide is selected from the group consisting of RGD, cyclic RGD (cRGD) and an RDG mimetic.

In an aspect of this invention, the hemocompatible and/or prohealing moiety comprises a phosphorylcholine.

In an aspect of this invention, the drug reservoir layer or the topcoat layer comprises a phosphorycholine moiety having the formula:

wherein L comprises a Linker and m and n have values from 0 to 1 such that m+n=1.

In an aspect of this invention, the drug reservoir layer polymer has a molecular weight from about 50,000 to about 500,000 Daltons.

In an aspect of this invention, the drug reservoir layer has a coating thickness from about 1 um to about 10 um.

In an aspect of this invention, the drug to polymer wt/wt ratio in the drug reservoir layer is from about 1.0:0.5 to about 1.0:10.0.

In an aspect of this invention, the drug dose is from about 5-200 microgram/$cm^2$ to about 20-100 microgram/$cm^2$.

In an aspect of this invention, the vascular disease is atherosclerosis.

In an aspect of this invention, the vascular disease is restenosis.

In an aspect of this invention, the vascular disease is vulnerable plaque

In an aspect of this invention, the vascular disease is peripheral vascular disease.

In an aspect of this invention, the vascular disease is late stent thrombosis.

DETAILED DESCRIPTION OF THE INVENTION

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts.

An implantable medical device specifically designed and intended solely for the localized delivery of a therapeutic agent is within the scope of this invention.

As used herein, "device body" refers to a fully formed implantable medical with an outer surface to which no coating or layer of material different from that of which the device itself is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what material it is made.

Implantable medical devices made of virtually any material, i.e., materials presently known to be useful for the manufacture of implantable medical devices and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

Implantable medical devices may also be made of polymers that are biocompatible and biostable or biodegradable, the latter term including bioabsorbable and/or bioerodable.

As used herein, "biocompatible" refers to a polymer that both in its intact, as synthesized state and in its decomposed state, i.e., its degradation products, is not, or at least is minimally, toxic to living tissue; does not, or at least minimally and reparably, injure living tissue; and does not, or at least minimally and/or controllably, cause an immunological reaction in living tissue.

Among useful biocompatible, relatively biostable polymers are, without limitation, polyacrylates, polymethacrylates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device useful with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an arterial wall thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As used herein, "optional" means that the element modified by the term may or may not be present. For example, without limitation, a device body (db) that has coated on it an "optional" primer layer (pl), a drug reservoir layer (dr), and an "optional" top-coat layer (tc) refers, without limitation, to any of the following devices: db+dr, db+pl+dr, db+dr+tc, and db+pl+dr+tc.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. Examples without limitation, of primers include acrylate and methacrylate polymers with poly(n-butyl methacrylate) being a presently preferred primer. Some additional examples of primers include, but are not limited to, poly(ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), and parylene-C.

As use herein, a material that is described as a layer "disposed over" an indicated substrate, e.g., without limitation, a device body or another layer, refers to a relatively thin coating of the material applied, preferably at present, directly to essentially the entire exposed surface of the indicated substrate. By "exposed surface" is meant that surface of the substrate that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. For the purpose of this invention, the drug reservoir layer also acts as rate-controlling layer. As used herein, "rate-controlling layer" refers to a polymer layer that controls the release of therapeutic agents or drugs into the environment. While any polymer may be used to construct a drug reservoir layer of this invention, in particular when a topcoat layer comprising hemocompatible and/or pro-healing moieties is used, in presently preferred embodiments of this invention, the drug reservoir layer comprises a high molecular weight copolymer of lactic acid, L-lactide, D,L-lactide or meso-lactide with ε-caprolactone or derivatives thereof, at least a portion of which is substituted with a hemocompatible and/or prohealing moiety; or, a blend of a high molecular weight copolymer of lactic acid, L-lactide, D,L-lactide or meso-lactide with ε-caprolactone or trimethylene carbonate with a low molecular weight copolymer of lactic acid, L-lactide, D,L-lactide or meso-lactide with ε-caprolactone or trimethylene carbonate at least a portion of which is substituted with a hemocompatible and/or prohealing moiety; or, a high molecular weight copolymer of lactic acid, L-lactide, D,L-lactide or meso-lactide with ε-caprolactone or derivatives thereof.

It is understood that many other biocompatible, hydrophobic polymers capable of being modified with hemocompatible and/or pro-healing moieties can be used as drug reservoir and/or topcoat layers of this invention. All such polymers are within the scope of this invention, the salient aspect of which is in fact the inclusion of the hemocompatible and/or pro-healing moieties in the outermost layer of the coating on an implantable medical device whether it be the drug reservoir layer, a separate rate-controlling layer or a topcoat layer.

As used herein, "hydrophobic" refers to a polymer that lacks an affinity for water. That is, it tends to repel water, to not dissolve in, mix with or be wetted by water or to do so only to a very limited degree and to not absorb water or, again, to do so only to a very limited degree. With regard to polymers, generally hydrophobicity increase with increasing alkyl content in the polymer backbone, that is, the greater the alkyl content in one or more of the constitutional units of the polymer. The hydrophobicity of a polymer may be characterized by determining the static contact angle of droplets of distilled water on a surface of the polymer. The greater the contact angle, the more hydrophobic the polymer. Generally speaking, a contact angle of greater than 90° indicates a hydrophobic polymer. The specifics or such measurements will not be presented here since they are well-known to those skilled in the art.

As used herein, "contact angle" is defined as an angle at the tangent of a droplet in a fluid phase that has taken an equilibrium shape on a solid surface under ambient condition.

As used herein, "hydrophobicity" can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

Accordingly, for the practice of the present invention, whether a material is hydrophobic or hydrophilic is relative. Between different materials, whichever has a lower Hildebrand value (δ) value compared to the δ value of the other is designated as a hydrophobic, and the material with higher Hildebrand value (δ) value is designated as a hydrophilic. In one embodiment, the δ value defining the boundary between hydrophobic and hydrophilic can be between about 9.9 and 10.1 $(cal/cm^3)^{1/2}$. According to this embodiment, hydrophobic is defined as having a δ value equal to or below about 9.9 $(cal/cm^3)^{1/2}$, and hydrophilic is defined as having a δ value of about 10.1 $(cal/cm^3)^{1/2}$ or higher. Materials having a δ value between about 9.9 and 10.1 $(cal/cm^3)^{1/2}$ can exhibit behavior characterized by both hydrophilic and hydrophobic materials. Such materials are defined as "amphiphilic." Measurements other than Hildebrand value for the determination of hydrophobicity are known to those skilled in the art and may be employed in the same manner as the Hildebrand value to achieve the same end.

Suitable hydrophobic polymers include, without limitation, poly(vinyl acetate), poly(ethylene-co-vinyl acetate), poly(vinyl acetals) such as poly(vinyl butyral) (e.g., BUTVAR), poly(meth)acrylates, for example, poly(methyl methacrylate), poly(ethyl methacrylate), poly(n-propyl methacrylate), poly(iso-propyl methacrylate), poly(n-butyl methacrylate), copolymers of butyl n-methacrylate with non-polar monomers (e.g., poly(ethyl methacrylate-co-n-butyl methacrylate)), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), styrene-butadiene-styrene triblock copolymers, styrene-ethylene/butylene-styrene triblock copolymers (e.g., KRATON available from Shell Oil Co. of Houston, Tex.), styrene-isobutylene-styrene triblock copolymers, parylene-C, organosilicon polymers (e.g., ELASTEON), and halogenated (e.g., fluorinated or chlorinated) polymers such as poly(vinyl chloride), poly(vinyl fluoride), poly(vinylidene chloride), poly(vinylidene fluoride) (e.g., KYNAR available from Atofina Chemicals, Inc. of Philadelphia, Pa.), poly(hexafluoropropene), poly(vinylidene fluoride-co-hexafluoropropene) (e.g., SOLEF available from Solvay S.A. of Brussels, Belgium), poly(ethylene-co-hexafluoropropene), and various grades of amorphous TEFLON, including polytetrafluoroethylene (available from E.I. Du Pont de Nemours & Co. of Wilmington, Del.), BUTVAR is a trade name of poly(vinyl butyral) (available from Solutia, Inc. of St. Louis, Mo.), ELASTEON is the trade name of the block copolymer of methylene diphenyl diisocyanate, 1,4-butanediol, polyhexamethyleneglycol, and a carbinol terminated polydimethylsiloxane (manufactured by AorTech Biomaterials Co. of Chatswood, Australia), poly[trimellitylimido-L-tyrosine-co-sebacic acid-co-1,3-bis(para-carboxyphenoxy)propane] p(TMIT-SBA-PCPP), poly[1,6-bis(para-carboxyphenoxy)-hexane-co-di-ortho-carboxyphenoxy sebacateanhydride] p(PCPX-OCPSA), poly[1,3-bis(para-carboxyphenoxy) propane-co-salicylic acid-co-sebacic acid] p(PCPP-SBA-SA), poly(maleic acid-co-sebacic acid), p(MA-SBA), poly(L-lactic acid-co-L-aspartic acid), p(LLA-LAspA), poly(DL-lactic acid-co-L-aspartic acid) p(DLLA-LAspA), poly(L-lactic acid) pLLA, poly(DL-lactic acid) pDLLA, poly(L-lactic acid-co-ethylene glycol) p(LLA-EG), poly(DL-lactic acid-co-ethylene glycol) p(DLLA-EG), poly(ethylene glycol-co-butylene terephthalate) p(EG-BT), poly(4-hydroxy-L-proline ester) p(HOXPE), poly(1,10-decanediol-co-L-lactic acid) p(DCD-LLA), poly(1,10-decanodiol-co-D,L-lactic acid) p(DCD-DLLA), poly(1,2,6-hexanetriol-co-trimethylorthoacetate) p(HTOL-TMAC), poly(hydroxybutyrate) (PHB), poly(hydroxyvalerate) (PHV), poly(hydroxy-butyratevalerate) (PHBV), poly(L-lactide-co-ε-caprolactone) and poly(L-lactide-co-trimethylene carbonate).

As used herein, "hemocompatible" refers to a property of a surface of a device to cause little, preferably no, harm to blood or blood components. In general, the tests set forth in ISO (international Organization for Standardization) 10993 may be employed to ascertain the level of hemocompatibility of a particular device of this invention.

As used herein, "prohealing" refers to a moiety that aids in the healing process at the site of implantation of a medical device of this invention. Useful pro-healing moieties include, without limitation, endothelial progenitor cells, nitric oxide, vascular endothelial growth and 17-b-estradiol.

As used herein, any words of approximation such as without limitation, "about," "essentially," "substantially" and the like mean that the element so modified need not be exactly that which is modified by the term but which would still be considered by one of ordinary skill in the art to be recognizable as that element. In general, for the purpose of this invention, this means that an element so modified can vary from the description by at least ±15% without exceeding the scope of this invention.

As used herein, the term "constitutional unit" refers to the repeating units that make up the polymer. For example, in the poly(L-lactide-co-ε-caprolactone) of this invention the constitutional units are —OCH(CH$_3$)C(=O)—, derived from L-lactide and —O(CH$_2$)$_5$C(=O)—, derived from ε-caprolactone. For the purposes of this invention the constitutional unit wt/wt ratio of a presently preferred polymer is from about 70:30 to about 50:50.

As used herein, "Linker" refers to a multifunctional moiety in which at least one functional group is capable of reacting with a functional group on the backbone of a polymer hereof and a different functional group capable of reacting with a functional group on a hemocompatible and/or pro-healing moiety so as to join or "link" the hemocompatible and/or prohealing group(s) to the polymer backbone.

As used herein, "and/or" in the phrase "hemocompatible and/or pro-healing" refers to either a chemical moiety that possesses both properties or to individual moieties that exhibit one or the other property. With regard to a hemocompatible and/or pro-healing polymer of this invention, the polymer may have the chemical moiety possessing both properties appended to its backbone, it may have an individual moiety exhibiting one of the properties appended to its backbone, it may have two different moieties, one possessing one of the properties and the second possessing the other property both appended to its backbone or any combination of the foregoing.

As used herein [[—Y—]$_n$/[—Z—]$_m$]$_x$ refers to a random, a regular alternating or a block, preferably at present a random, copolymer. As use herein, the letters "n" and "m" connote mole fractions of the constitutional units Y and Z, that is, m and n each have values from 0 to 1 such that m+n=1, where m is from about 0.01 to about 0.99 and n is from about 0.99 to about 0.01. It is presently preferred that m is from about 0.5 to about 0.8. It is most presently preferred that the m is from about 0.65 to about 0.75. The letter "x" connotes sequence multiplicity, that is, the number of repeats of the entity within the outside brackets in the polymer.

As used herein, a "topcoat layer" refers to an outermost layer, that is, a layer that is in contact with the external environment and that is coated over all other layers. The topcoat layer may be a separate layer distinct from drug reservoir layer or the drug reservoir layer may itself be the outermost layer and therefore constitute the topcoat layer of a coating, if the drug reservoir layer contains hemocompatible and/or prohealing moieties. A separate topcoat layer may be applied to provide better hydrophilicity to the device, to better lubricate the device or merely as a physical protectant of the underlying layers. If the drug reservoir layer comprises a high molecular weight copolymer of lactic acid, L-lactide, D,L-lactide or meso-lactide with ε-caprolactone or derivatives thereof, the implantable medical device further has a topcoat layer comprising a low molecular weight copolymer of lactic acid, L-lactide, D,L-lactide or meso-lactide with ε-caprolactone or trimethylene carbonate at least a portion of which is substituted with a hemocompatible and/or prohealing moiety. For the purposes of this invention, the outermost layer, be it the drug reservoir or the topcoat layer must comprises a hemocompatible and/or prohealing moiety. In a presently preferred embodiment, the hemocompatible and/or prohealing moiety comprises polyhydroxyalkyl, phosphoryl choline and/or peptides. Other natural or recombinant polymers can also provide prohealing properties which include, but not limited to, elastin, collagen, laminin, and polysaccharide.

Presently preferred polymers used to construct either a drug reservoir layer or a topcoat layer of this invention, include, but not limited to, polymers having a hydrophobic polymer backbone with hydrophilic, hemocompatible and/or prohealing pendant groups. The presently preferable polymer used to construct hydrophobic polymer backbone of this invention is a copolymer comprising at least two monomers one of which is selected from the group consisting of L-lactide, D-lactide, D,L-lactide and meso-lactide. The second monomer selected from the group consisting of lactone, ε-caprolactone, δ-valerolactone, 1,4-dioxan-2-one, 1,5-dioxepan-2-one, 1,4,6-trioxaspiro[4.4]nonane and trimethyl carbonate. Presently preferred hydrophobic polymer backbone of this invention are poly(L-lactide-co-ε-caprolactone) and poly(L-lactide-co-trimethylene carbonate).

The combination of biocompatibility and biodegradability with the physical strength provided by poly(L-lactide-co-ε-caprolactone) is useful for medical device application. However, the simplicity of the polymer presents limitations in terms of functionality and physical properties, mainly because of its hydrophobic nature. Branching and pendant functionalization of hydrophobic polymers provides a unique opportunity to alter physical and chemical properties by distributing functionality along the polymer backbone. Pendant functionalization of the polymers can be achieved by polymerization of functionalized lactones or post polymerization modification or a combination of these two methods. Branching and/or pendant functionality can be used to tune physical and chemical properties, including viscosity, solubility, hydrophilicity, adhesion and blood compatibility. The hydrophobic polymers can be modified to have pendant groups which are hydrophilic. These hydrophilic groups are hemocompatible and/or prohealing moieties. Suitable hydrophilic, hemocompatible and/or prohealing moieties include, without limitation, polyhydroxyalkyl, phosphoryl choline, and peptides.

Suitable examples of polyhydroxyalkyls include, without limitation, glycerol, sorbitol, mannitol, a glycol, a polyalkylglycol and a polyglycol.

An advantage of having phosphoryl choline (PC) as the hemocompatible and pro-healing moiety lies in its surface chemistry. That is, PC has a zwitterionic functionality that mimics the outer blood-contacting surface of the lipid bilayer structure in blood corpuscles. PC possesses numerous beneficial properties such as hemocompatibility and/or prohealing characteristics, non-thrombogenicity, arterial tissue acceptance and long-term in vivo stability. PC-containing polymers are extremely hydrophilic and associate a large number of water molecules because of the zwitterionic nature of the PC head group. Further, coatings comprising PC-containing polymers in the outermost layer tend to not invoke adverse inflammatory response.

The polypeptide Arg-Gly-Asp (RGD) has been demonstrated to be a bioactive factor for human endothelial cell attachment and therefore is expected to exhibit prohealing characteristics. In addition to RGD itself, cyclic RGD (cRGD) and RGD mimetics and small molecules capable of binding as does RGD to other adhesion receptors differentially expressed on the endothelial cells are within the scope of this invention. RGD mimetics can be prepared, without limitation by modification of RGD or cRGD. Peptide synthesis including the synthesis of peptide mimetics, is well documented and can be readily achieved using, for example, combinatorial chemistry. Some examples of cRGD or RGD mimetics include $V_3$ antagonists such as IIb/IIIb antagonists (B.S. Coller, *Thromb. Haemost.* 2001, 86:427-443 (Review)), one example of which is Abciximax (R. Blindt, *J. Mol. Cell. Cardiol.* 2000, 32:2195-2206), XJ 735 (S. S. Srivastva et al., *Cardiovasc. Res.* 1997, 36:408-428), anti-3-integrin antibody F11, cRGD (M. Sajid et al., *Am. J. Physiol. Cell Physiol.*, 2003, 285:C1330-1338), and other sequences such as laminin derived SIKVAV (M.H. Fittkau et al., *Biomaterials*, 2005, 26:167-174), laminin derived YIGSR (S. Kouvroukoglou et al., *Biomaterials*, 2000, 21:1725-1733), KQAGDV, and VAPG (B. K. Mann, *J. Biomed. Mater. Res.* 2002, 60:86-93).

The presently preferable polymers of this invention to which hemocompatible and/or prohealing moieties can be appended are poly(L-lactide-co-ε-caprolactone) and poly(L-lactide-co-trimethylene carbonate). The presently preferable hydrophilic, hemocompatible and/or prohealing moieties used in this invention are polyhydroxyalkyl, phosphoryl choline, and peptides.

In addition to the comprising a polymer having hemocompatible and/or prohealing properties, a coating on an implantable medical device of this invention may also contain in the drug reservoir layer and possibly in the topcoat layer one or more therapeutic agents.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, "treating" refers to the administration of a therapeutically effective amount of a therapeutic agent to a patient known or suspected to be suffering from a vascular disease. A "therapeutically effective amount" refers to that amount of a therapeutic agent that will have a beneficial affect, which may be curative or palliative, on the health and well-being of the patient with regard to the vascular disease with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery, or loss of organ function if the artery is peripheral.

"Restenosis" refers to the re-narrowing or blockage of an artery at or near the site where angioplasty or another surgical procedure was previously performed to remove a stenosis. It is generally due to smooth muscle cell proliferation and, at times, is accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to smooth muscle cell proliferation. There were also issues of acute reclosure due to vasospasm, dissection, and thrombosis at the site of the procedure. Stents eliminated acute closure from vasospasm and greatly reduced complications from dissections. While the use of IIb-IIIa anti-platelet drugs such as abciximab and epifabatide, which are anti-thrombotic, reduced the occurrence of post-procedure clotting (although stent placement itself can initiate thrombosis). Stent placement sites are also susceptible to restenosis due to abnormal tissue growth at the site of implantation. This form of restenosis tends also to occur at 3 to 6 months after stent placement but it is not affected by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time. To date these stents comprised delivery interfaces (lengths) that are less than 40 mm in length and, in any event, have delivery interfaces that are not intended, and most often do not, contact the luminal surface of the vessel at the non-afflicted region at the periphery of the afflicted region.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque is exposed to blood, with the potential of causing a potentially fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage-derived enzyme degradation can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

"Thrombosis" refers to the formation or presence of a blood clot (thrombus) inside a blood vessel or chamber of the heart. A blood clot that breaks off and travels to another part of the body is called an embolus. If a clot blocks a blood vessel that feeds the heart, it causes a heart attack. If a clot blocks a blood vessel that feeds to brain, it causes a stroke.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

Suitable therapeutic agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives and analogs include 40-O-(2-hydroxyethyl)rapamycin (EVEROLIMUS®), 40-O-(3-hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Suitable antiallergic agents include, without limitation, permirolast potassium. Other suitable bioactive agents include, without limitation, alpha-interferon, genetically engineered epithelial cells, dexamethasone and its derivatives, rapamycin derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethylrapamycin, and 40-O-tetrazolylrapamycin, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Preferred therapeutic agents include corticosteroids, everolimus, zotarolimus, sirolimus, sirolimus derivatives, paclitaxel, bisphosphonates, ApoA1, mutated ApoA1, ApoA1 milano, ApoA1 mimetic peptides, ABC A1 agonists, anti-inflammatory agents, anti-proliferative agents, anti-angiogenic agents, matrix metalloproteinase inhibitors and tissue inhibitors of metalloproteinases.

EXAMPLES

The embodiments of the present invention are further illustrated by the following examples. The examples are provided for illustrative purposes only and are not intended nor should they be construed as limiting the scope of this invention in any manner whatsoever.

Example 1

A composition was prepared by placing poly(L-lactide-co-ε-caprolactone) (0.12 g), chloroform (4.6848 g) and tricholoroethane (1.17 g) in a tightly closed glass bottle and stirring at 250 rpm for 2 hours. Everolimus (0.0245 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 6 um.

Example 2

A composition was prepared by placing poly(L-lactide-co-ε-caprolactone) (0.12 g), chloroform (4.67 g) and tricholoroethane (1.17 g) in a tightly closed glass bottle and stirring at 250 rpm for 2 hours. Everolimus (0.0408 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:3. The drug dose is about 100 microgram/cm$^2$. The drug reservoir layer coating thickness is 4 um.

Example 3

A composition was prepared by placing poly(L-lactide-co-trimethylene carbonate) (0.06 g) and tricholoroethane (2.928 g) in a tightly closed glass bottle and stirring 250 rpm for 2 hours. Everolimus (0.01224 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 6 um.

Example 4

A composition was prepared by placing poly(L-lactide-co-trimethylene carbonate) (0.06 g) and tricholoroethane (2.928 g) in a tightly closed glass bottle and stirring at 250 rpm for 2 hours. Everolimus (0.01224 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 50 microgram/cm$^2$. The drug reservoir layer coating thickness is 6 um.

Example 5

A composition was prepared by placing poly(L-lactide-co-ε-caprolactone) (0.12 g), chloroform (4.6848 g) and tricholoroethane (1.17 g) in a tightly closed glass bottle and stirring at 250 rpm for 2 hours. Phosphoryl choline (0.2 g) in methanol (2.44 g) and dimethylacetamide (2.44 g) was added to the reaction mixture and mixture further stirred for 2 hours. Everolimus (0.0444 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 6 um.

Example 6

A composition was prepared by placing poly(L-lactide-co-trimethylene carbonate) (0.12 g) chloroform (4.6848 g) and tricholoroethane (1.17 g) in a tightly closed glass bottle and stirring at 250 rpm for 2 hours. Phosphoryl choline (0.2 g) in methanol (2.44 g) and dimethylacetamide (2.44 g) was added to the reaction mixture and mixture further stirred for 2 hours. Everolimus (0.0444 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 6 um.

Example 7

A composition was prepared by placing poly(L-lactide-co-ε-caprolactone) (0.2 g), acetone (8 g) and methylisobutylketone (2 g) in a tightly closed glass bottle and stirring at 560 rpm for 2 hours. cRGD (0.4 g) was added to the reaction mixture and mixture further stirred for 2 hours. Everolimus (0.06 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 56 um.

Example 8

A composition was prepared by placing poly(L-lactide-co-ε-caprolactone) (0.2 g), acetone (8 g) and methylisobutylketone (2 g) in a tightly closed glass bottle and stirring at 560 rpm for 2 hours. RGD (0.4 g) was added to the reaction mixture and mixture further stirred for 2 hours. Everolimus (0.06 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 56 um.

Example 9

A composition was prepared by placing poly(L-lactide-co-trimethylene carbonate) (0.2 g), acetone (8 g) and methylisobutylketone (2 g) in a tightly closed glass bottle and stirring at 560 rpm for 2 hours. cRGD (0.4 g) was added to the reaction mixture and mixture further stirred for 2 hours. Everolimus (0.06 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 56 um.

Example 10

A composition was prepared by placing poly(L-lactide-co-trimethylene carbonate) (0.2 g), acetone (8 g) and methyl-isobutylketone (2 g) in a tightly closed glass bottle and stirring at 560 rpm for 2 hours. RGD (0.4 g) was added to the reaction mixture and mixture further stirred for 2 hours. Everolimus (0.06 g) was then added to the reaction mixture and the reaction mixture was stirred at 500 rpm for an additional 2 minutes. The first composition was applied onto the stent and dried to form a drug-polymer layer.

The composition was applied onto a stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is about 100 microgram/cm$^2$. The drug reservoir layer coating thickness is 56 um.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed:

1. An implantable medical device comprising:
    a device body;
    an optional primer layer disposed over the device body;
    a drug reservoir layer disposed over the device body or the primer layer, if opted, wherein the drug reservoir layer comprises:
    i) a high molecular weight copolymer of L-lactide, D,L-lactide, or meso-lactide with e-caprolactone or trimethylene carbonate, at least a portion of which is substituted with a pendant hemocompatible and/or a prohealing moiety; or,
    ii) a blend of a high molecular weight copolymer of L-lactide, D,L-lactide, or meso-lactide with e-caprolactone or trimethylene carbonate and a low molecular weight copolymer of lactic acid or glycolic acid with e-caprolactone or trimethylene carbonate at least a portion of which is substituted with a pendant hemocompatible and/or prohealing moiety; or
    iii) a high molecular weight copolymer of L-lactide, D,L-lactide, or meso-lactide with e-caprolactone or trimethylene carbonate, and a topcoat layer comprising a low molecular weight polymer of lactic acid or glycolic acid with e-caprolactone or trimethylene carbonate at least a portion of which is substituted with a pendant hemocompatible and/or prohealing moiety;
    wherein the drug reservoir layer or the topcoat layer of i), ii) or iii) comprises the copolymer of i), ii) or iii) having the formula:

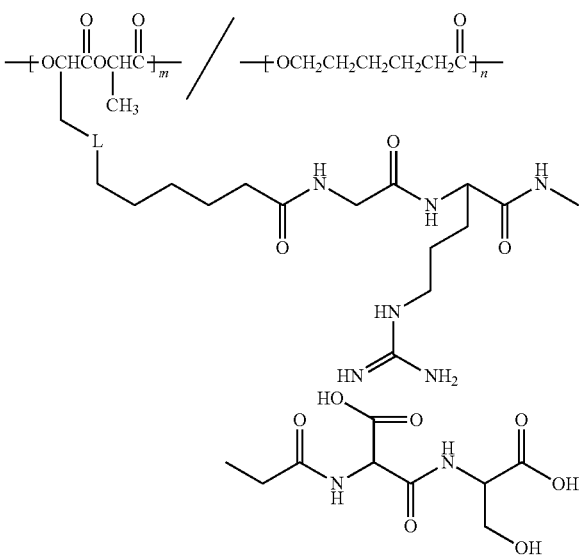

wherein:
L comprises a Linker; and,
m is from about 0.01 to about 0.99;
n is from about 0.99 to about 0.01; and
n+m=1.

2. The implantable medical device of claim 1, wherein the m is from about 0.5 to about 0.8.

3. The implantable medical device of claim 2, wherein the m is from about 0.65 to about 0.75.

* * * * *